United States Patent
Howie et al.

(10) Patent No.: US 7,044,978 B2
(45) Date of Patent: May 16, 2006

(54) POSITIONER AND METHOD FOR A FEMORAL HIP IMPLANT

(75) Inventors: Donald W. Howie, Tennyson (AU); David M. Blakemore, Warsaw, IN (US); Stephen H. Hoag, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/694,068

(22) Filed: Oct. 27, 2003

(65) Prior Publication Data

US 2005/0090904 A1   Apr. 28, 2005

(51) Int. Cl.
*A61F 2/28* (2006.01)

(52) U.S. Cl. ............... 623/23.48; 623/23.26; 623/23.19; 606/95

(58) Field of Classification Search ............ 606/92–95; 623/23.19–23.27, 23.48
See application file for complete search history.

(56) References Cited

U.S. PATENT DOCUMENTS

| | | | | |
|---|---|---|---|---|
| 4,698,063 A | * | 10/1987 | Link et al. ................ | 623/23.22 |
| 5,425,768 A | * | 6/1995 | Carpenter et al. ........ | 623/23.48 |
| 5,571,202 A | * | 11/1996 | Mathys et al. ........... | 623/23.27 |
| 5,702,485 A | * | 12/1997 | Burke et al. ............. | 623/23.21 |
| 2002/0052661 A1 | * | 5/2002 | Spotorno et al. ........ | 623/23.48 |

OTHER PUBLICATIONS

Brochure © 2002 Zimmer, Inc., VerSys® Hip System, Advocate™, V-Lign® and V-Lign® Cemented Hip Prosthesis.
Brochure © 1996 Zimmer, Inc., The CPT® Hip System, Primary Surgical Technique, Collarless Polished Taper.
Brochure © 2002 Zimmer, Inc., VerSys® Hip System, Traditional Design, Innovative Features., Advocate™ Hip Prosthesis.

* cited by examiner

*Primary Examiner*—Bruce Snow
(74) *Attorney, Agent, or Firm*—Cary Reeves; Jonathan Feuchtwang

(57) ABSTRACT

The present invention provides a positioner for controlling the position of a femoral hip implant within the intramedullary canal of a femur.

17 Claims, 1 Drawing Sheet

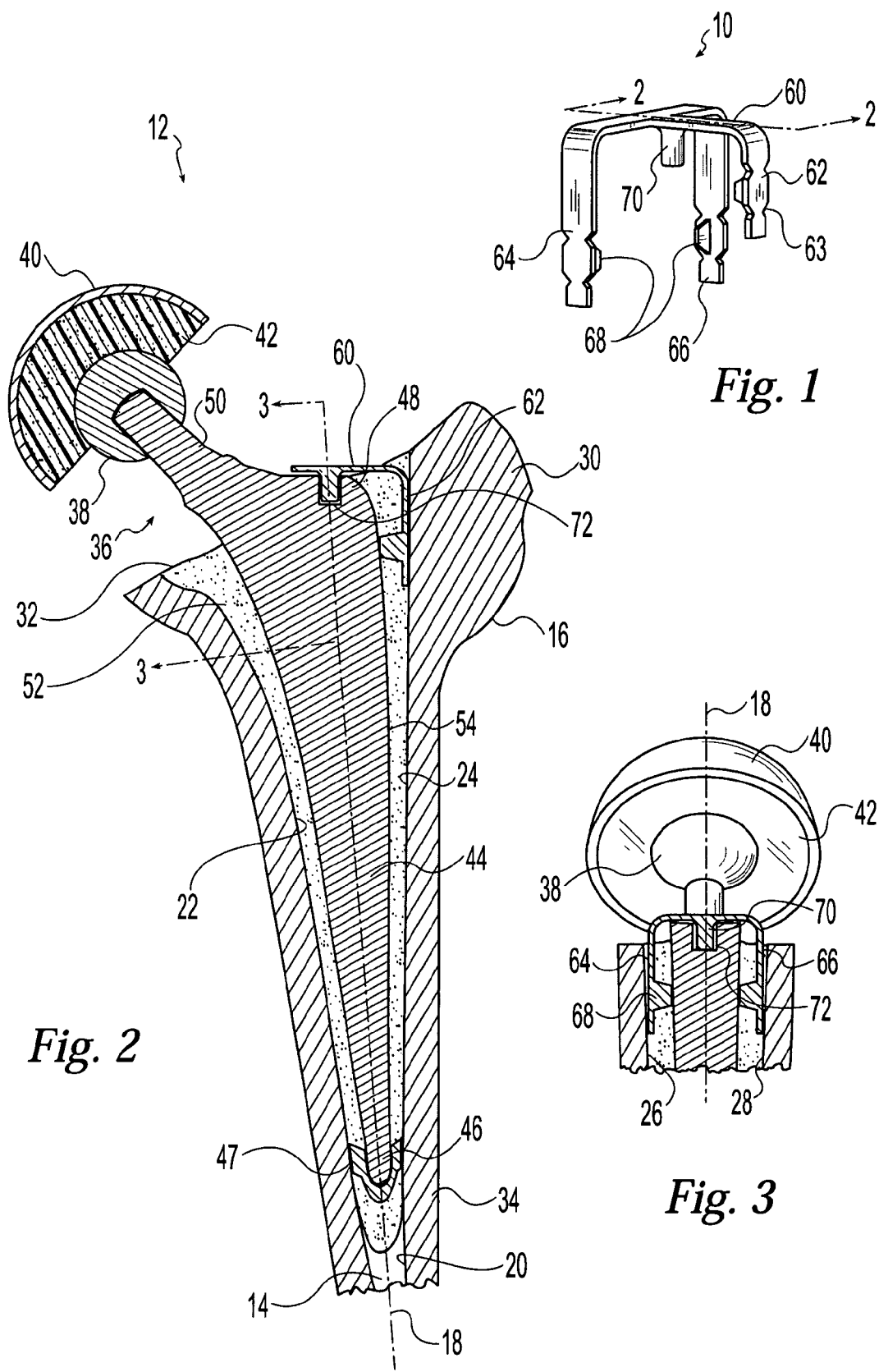

POSITIONER AND METHOD FOR A FEMORAL HIP IMPLANT

BACKGROUND

Total hip arthroplasty is often used to restore function to a diseased or injured hip joint. Positions and directions relative to the hip joint may be described in terms of proximal being nearer the hip joint, distal being further from the hip joint, anterior being nearer the front of the body, posterior being nearer the back of the body, medial being nearer the centerline of the body, and lateral being further from the center line of the body. In total hip arthroplasty, the surfaces of the femur and pelvis are cut away and replaced with substitute implants. In a typical case, the implants include a hip stem component, a femoral head component, an acetabular component and bone cement.

The femoral bone is prepared by reaming the femoral canal down into the bone along an axis from a proximal position near the hip joint at the upper end of the femur toward a distal position nearer the knee joint at the lower end of the femur. The pelvis is prepared by reaming the acetabulum. The implants may be placed directly in contact with the prepared bone surfaces for bony fixation of the implant. Alternatively, bone cement may be introduced into the prepared canal and acetabulum so that it hardens around and locks the components in place.

The hip stem component includes a stem portion extending down into the intramedullary canal of the femur and a neck portion extending away from the femur to support the femoral head component. Some cemented hip stem designs rely on a tapered and highly polished exterior surface for use with cement to permit subsidence of the stem into the cement when the cement undergoes load induced deformation in use. By subsiding with the deforming cement, the implant maintains intimate contact with the cement.

Occasionally an undesirable upward force can occur that may withdraw a femoral component from the femoral canal. For example, if the femoral head dislocates from the acetabular component, a surgeon may attempt to reposition them by manipulating the patient's leg in a process known as a closed reduction. Sometimes, during this procedure, the femoral head can catch on the edge of the acetabular component causing the femoral implant to be lifted up such that surgical intervention is required.

Furthermore, for a cemented implant, positioning the femoral component in the correct orientation within the cement is important for proper biomechanical functioning and long term stability of the implants. Proper placement results in a uniform and strong cement mantle around the component. Proper placement further results in appropriate loading of the implants. Femoral components, especially collarless ones, are sometimes placed at the wrong angle in the mediolateral direction. The typical situation is a varus placement in which the angle between the neck and femoral axis is too shallow.

SUMMARY

The present invention provides a positioner for controlling the position of a femoral hip implant within the intramedullary canal of a femur.

In one aspect of the invention, a positioner for implantation adjacent a femoral hip implant retains the femoral hip implant in the femoral canal. The positioner prevents the femoral hip implant from rising out of the femoral canal beyond a predetermined position.

In another aspect of the invention, the positioner prevents the femoral hip implant from rising while permitting subsidence of the femoral hip implant down into the femoral canal.

In another aspect of the invention, a positioner includes a first member and a second member. The first member extends over a portion of the implant such that it limits upward axial motion of the femoral hip implant and permits downward axial motion of the femoral hip implant. The second member extends from the first member and secures the positioner adjacent to the femoral canal.

In another aspect of the invention, a femoral hip system includes a femoral hip implant having a stem for insertion in a femoral canal and a positioner. The positioner has an anchor member securing it in the femoral canal adjacent the femoral hip implant and a retention member engageable with a portion of the femoral hip implant such that it blocks upward motion of the implant out of the canal while permitting downward motion of the implant into the canal.

In another aspect of the invention, a positioner includes an "L"-shaped body having a first leg positionable over a portion of the femoral hip implant relative to the canal axis. A second leg is simultaneously positionable adjacent the canal wall to maintain a predetermined spacing between the femoral hip implant and the canal wall.

In another aspect of the invention, a method includes providing a femoral hip implant configured to fit within a femoral canal; inserting cement into the femoral canal; inserting the femoral hip implant into the cement in the femoral canal; and inserting an implant positioner into the cement so that it becomes firmly attached to the cement upon hardening of the cement and permits the femoral hip implant to subside down into the cement but prevents it from rising up out of the cement beyond a predetermined position by engagement with the implant positioner.

BRIEF DESCRIPTION OF THE DRAWINGS

Various embodiments of the present invention will be discussed with reference to the appended drawings. These drawings depict only illustrative embodiments of the invention and are not to be considered limiting of its scope.

FIG. 1 is a perspective view of an illustrative positioner according to the present invention;

FIG. 2 is a side section view taken along line 2—2 of FIG. 1 and further showing the positioner of claim 1 in combination with joint replacement implants; and FIG. 3 is a side section view taken along line 3—3 of FIG. 2.

DESCRIPTION OF THE ILLUSTRATED EMBODIMENTS

A positioner is provided to control the position of a femoral hip implant within the intramedullary canal. The positioner may control the radial position of the femoral implant and/or the axial position by limiting movement of the femoral implant along the femoral axis.

The positioner may prevent the femoral hip implant from rising out of the femoral canal beyond a predetermined position while permitting subsidence of the femoral hip implant into the femoral canal. The positioner may prevent any upward motion of the implant once it is inserted or it may allow a limited amount of upward motion. The positioner may allow unimpeded or a predetermined amount of subsidence into the femoral canal. The positioner may be anchored to the bone of the femoral canal and/or anchored in cement placed within the femoral canal. The positioner may be configured for use with a hip stem implant having a polished and tapered exterior surface. Such a surface permits the implant to move relative to the cement such that it subsides distally into the cement under load. For example, the positioner may be anchored in cement to limit upward motion of the implant relative to the cement while permitting the implant to subside into the cement in response to axial loading.

The positioner may include a first member, or retention member, overlying a portion of the implant in the direction of the longitudinal axis of the femoral canal so that the implant is prevented from rising by abutment against the overlying portion. The retention member may extend over the top of the implant and/or over an intermediate portion of the implant. The positioner may include multiple members with one or more retention members overlying a portion of the implant and one or more second members, or anchor members, extending into the bone and/or cement to anchor the positioner. The members may angle away from one another and/or form an "L", "U", saddle, and/or other suitable shape. The individual members may have a round, rectangular, straight, tapered, and/or any other suitable cross sectional shape. The members may engage the femoral implant to retain the positioner on the femoral implant until they are inserted into the femoral canal. The members may fit loosely, fit tightly, be elastically biased against, or otherwise engage the implant. The members may be adjacent the implant or include third members, or spacing members, in the form of projections that engage the implant and space the members from the implant to allow cement to be positioned between the implant and members. For example, the positioner may include a body with a plurality of anchor members in the form of legs extending downwardly and a spacing member in the form of a projection extending inwardly from each leg that is biased to elastically grip the implant.

The positioner may control the radial position of the femoral hip implant relative to the wall of the femoral canal. The positioner may space the implant from the anterior, posterior, medial, and/or lateral aspects of the canal wall. The positioner may engage the implant initially when the implant and positioner are inserted into the femoral canal. The positioner may control the radial position of the implant during this initial period and then subsequently, under physiologic loads of patient use, permit the implant to move axially away from the positioner. For, example the positioner may maintain the radial position of the implant within the femoral canal while cement hardens around the implant and then, in use, allow the implant to subside into the cement under physiologic loads. The positioner may include a first portion engageable with the top of the implant and a second portion engageable with the wall of the femoral canal to space the implant a predetermined distance from the wall. For example, the first portion may include a boss extending downwardly to engage an opening in the top of the implant. The positioner may include members extending along the anterior, posterior, medial, and lateral sides of the implant to space the implant from the wall of the femoral canal. The members may each include a tab engaging the side of the implant to space the members from the implant to permit cement to be positioned between the members and the implant. The positioner may also prevent the implant from rising out of the femoral canal beyond a predetermined position.

The positioner may include metal, ceramic, polymer, and/or other suitable biocompatible materials. For example, a polymer implant may include polyester, polyethylene, polyamides, polymethylmethacrylate, polyglycolic acid, polylactic acid, and/or other suitable nonresorbable and resorbable polymers. The positioner may include a polymer compatible with one or more polymers contained in a bone cement to be used with the positioner so that the positioner bonds to the cement and reduces stresses at the positioner/cement interface. For example, the positioner may include a polymethylmethacrylate polymer for use with cement including polymethylmethacrylate such that the positioner bonds to the cement.

FIGS. 1 through 3 depict an illustrative positioner 10 for controlling the position of a femoral component of a hip implant 12 within a femoral canal 14 of a femur 16. The femoral canal 14 includes a longitudinal axis 18 and a wall 20 surrounding the canal 14. The wall 20 has medial 22, lateral 24, anterior 26, and posterior 28 aspects. The femur 16 has a proximal portion 30 adjacent the opening 32 of the canal 14 and a distal portion 34 spaced downwardly from the proximal portion 30. The hip implant 12 includes a femoral component 36, a head 38, an acetabular shell 40, and an acetabular liner 42. The femoral component 36 is positioned within the canal 14 and supports the head 38. The acetabular shell 40 is positioned within the pelvis (not shown) and supports the acetabular liner 42. The head 38 articulates with the acetabular liner 42 to restore joint function. The femoral component 36 includes a stem 44 having a distal tip 46 positioned deep within the canal 14 and a proximal shoulder 48 positioned near the opening 32 of the canal 14. A neck 50 projects from the shoulder 48 to support the head 38. A distal stem positioner 47 helps centralize the distal tip 46 within the canal 14.

The illustrative femoral component 36 is embedded in cement 52 within the canal 14 and includes a polished and tapered exterior surface 54 permitting the femoral component 36 to move relative to the cement 52 after the cement has cured. Thus, the illustrative femoral component 36 may subside distally into the cement 52 under load to maintain intimate contact with the cement 52 even if the cured cement 52 deforms in use.

The positioner 10 includes a first member, or retention member 60, positionable over a portion of the femoral component 36 to prevent the femoral component 36 from rising out of the femoral canal beyond a predetermined position. In the illustrative embodiment, the retention member 60 is positioned over the shoulder 48 of the implant. However it is contemplated that the retention member 60 may be positioned over other portions of the femoral component 36 relative to the canal 14 axis 18 so that the femoral component 36 is prevented from rising from the canal 14 by abutment against the retention member 60. For example, the retention member 60 may be positioned over a projection anywhere along the stem 44. Alternatively, the positioner 10 may include a portion that fits within a recess in the stem 44.

The positioner 10 further includes a second member, or anchor member 62, for anchoring the retention member 60 relative to the canal 14 and/or cement 52. In the illustrative embodiment, the anchor member 62 extends at an angle from the retention member 60 and is embedded in the cement 52 to anchor the retention member 60 relative to the cement 52. However, the anchor member 62 may also be anchored in bone, for example by driving it into the femur 16 adjacent the canal 14 and thus anchor the retention member 60 relative to the canal 14. Scallops 63 in the anchor member 62 create a positive engagement with the cement 52 and/or femur 16 to enhance the fixation of the anchor member 62.

The illustrative positioner 10 further includes anterior 64 and posterior 66 members, or legs, extending from the retention member 60 and/or anchor member 62 to grip the femoral component 36. In the illustrative embodiment, the anterior 64 and posterior 66 legs are elastic and are biased inwardly to grip the femoral component 36. However, other means for gripping the implant are contemplated and fall within the scope of the present invention. The anterior 64 and posterior 66 members may be embedded in the cement 52 as shown to assist in anchoring the retention member 60.

The positioner 10 further includes a spacing member in the form of a boss 70 projecting downwardly from the retention member 60 to engage a recess 72 in the shoulder of the femoral component 36 in radial force transmitting relationship. The boss 70 helps to maintain the positioner 10 in proper orientation relative to the femoral component 36. Furthermore, the radial spacing of the boss 70 and one or more of the legs 62, 64, 66 maintains a predetermined spacing between the femoral component 36 and canal 14 wall 20. In the illustrative embodiment, the boss 70 and anchor member 62 form an "L"-shaped spacer with a retention member 60 positionable over and engageable with a portion of the femoral component 36 and a anchor member 62 positionable adjacent the canal 14 wall 20 to space the femoral component 36 from the lateral aspect 24 of the canal 14 wall 20. Where present, the anterior 64 and posterior 66 legs may likewise provide a predetermined radial spacing from the anterior 26 and posterior 28 aspects of the canal 14 wall 20. In the illustrative embodiment, the engagement of the retention member 60 and femoral component 36 is shown as a male boss 70 on the positioner 10 and a female recess 72 on the femoral component 36. However, it is contemplated that these may be reversed so that a male feature on the femoral component 36 engages a female feature on the positioner 10. Likewise, other engagement features providing for radial spacing are contemplated and fall within the scope of the present invention.

The lateral 62, anterior 64, and posterior 66 legs further include spacing members in the form of projections, or tabs 68, to space the members from the femoral component 36 and allow the cement 52 to be positioned between the legs 62, 64, 66 and the femoral component 36 so that the cement 52 makes direct contact with the femoral component 36. In addition, the tabs 68 may project a sufficient predetermined distance to substantially fill the space between the femoral component 36 and the canal 14 wall 20 and act to radially space the femoral component 36 from the canal 14 wall 20. The tabs 68 and boss 70 may be separately used or used in combination as shown.

In the illustrative embodiment, the positioner 10 is a unitary, "T"-shaped construct with legs projecting downwardly from the ends of the "T" and the boss 70 projecting downwardly from the intersection of the "T". The illustrative positioner 10 has a flat, rectangular cross-section throughout. However, other configurations and cross-sectional shapes are contemplated and fall within the scope of the present invention. In the illustrative embodiment, the positioner 10 is injection molded from an acrylic polymer. Such a positioner may be made from processes including machining from solid stock, injection molding, stamping and bending, and/or other suitable processes.

In use, the femur is prepared by creating an opening 32 into the femoral canal 14 and reaming the canal 14 to a suitable size to receive the femoral component 36. Liquid bone cement 52 is introduced into the canal 14 and the femoral component 36 is inserted into the cement 52. The positioner 10 is inserted into the cement 52 so that it becomes firmly attached to the cement 52 upon hardening of the cement 52. Alternatively, the positioner may be attached to the femur 16 adjacent the canal 14, with or without cement, for example, by driving one or more of the legs 62, 64, 66 into the bone. The positioner 10 can be inserted simultaneously with or after the femoral component 36. If the positioner 10 is being used to radially position the femoral component 36, the positioner 10 is engaged with the femoral component 36, such as by inserting the boss 70 into the recess 72 and/or clipping one or more of the legs 62, 64, 66 around the femoral component 36. The femoral component 36 is then radially adjusted so that the positioner 10 engages the canal 14 wall 20 to space the femoral component a predetermined distance from the wall 20. For example, the femoral component 36 is pushed laterally until the lateral leg 62 is pressed against the lateral aspect 24 of the canal 14. Once the positioner 10 is firmly attached to the cement 52 and/or femur 16, it will prevent the femoral component 36 from rising up out of the canal 14 beyond a predetermined position as the femoral component 36 abuts the positioner 10. However, the positioner 10 permits the femoral component 36 to subside down into the canal 14.

Although embodiments of implants and their use have been described and illustrated in detail, it is to be understood that the same is intended by way of illustration and example only and is not to be taken by way of limitation. Accordingly, variations in and modifications to the implants and their use will be apparent to those of ordinary skill in the art, and the following claims are intended to cover all such modifications and equivalents.

What is claimed is:

1. A femoral hip implant for a femoral canal, the femoral canal having a canal wall with anterior, posterior, medial, and lateral aspects and a longitudinal axis along the femoral canal from a proximal position near the hip joint to a distal position nearer the knee joint, the femoral hip implant comprising:

a stem having a proximal end, a distal end, and a longitudinal axis extending therebetween, the stem having a polished and tapered exterior surface that permits the implant to subside distally into a cured cement mantel under load;

a positioner, the positioner being removably engageable with the stem, the positioner including means for preventing the stem from rising proximally beyond a predetermined position by abutment of the stem against the positioner while permitting distal subsidence of the stem; and means for anchoring the means for preventing relative to a femoral canal, the positioner comprising a body including first and second members extending at an angle from one another, the means for preventing including the first member and the means for anchoring including the second member, the first member being positionable proximally over a portion of the stem while the second member is simultaneously positionable along the exterior surface of the stem between the stem and the canal wall, the second member being anchorable in a cement mantel between the stem and the canal wall; and a head mounted on the stem, the head being engageable with a pelvic portion of the hip joint to provide articulating joint function, the means for preventing the stem from rising being able to prevent the stem from rising while permitting the stem to subside during articulation of the joint in use by a patient.

2. The femoral hip implant of claim 1 further comprising means for spacing the stem a predetermined distance from the lateral aspect of the femoral canal.

3. The femoral hip implant of claim 2 wherein the means for spacing comprises a spacing member connected to the body a predetermined distance from the second member, the spacing member being engageable with the stem and the second member being engageable with the lateral aspect of the femoral canal to maintain a predetermined spacing between the stem and the lateral aspect of the femoral canal.

4. The femoral hip implant of claim 3 wherein the spacing member comprises a projection extending medially from the second member toward the stem.

5. A positioner for retaining a femoral hip implant in a femoral canal, the femoral canal having anterior, posterior, medial, and lateral aspects and a longitudinal axis along the femoral canal from a proximal position near the hip joint to a distal position nearer the knee joint, the femoral hip implant being surrounded at least in part by cement positioned between the femoral hip implant and the femoral canal, the femoral hip implant having a longitudinal axis that in use is approximately parallel to the femoral canal longitudinal axis, and a polished and tapered exterior surface that permits the implant to move relative to the cement and therefore to subside distally into the cement under load, the positioner comprising:
  means for preventing the femoral hip implant from rising out of the femoral canal beyond a predetermined position while permitting subsidence of the femoral hip implant distally into the cement;
  means for anchoring the means for preventing relative to the femoral canal;
  a body including first and second members extending at an angle from one another, the means for preventing including the first member and the means for anchoring including the second member, the first member being positionable over a portion of the femoral hip implant, the second member being positionable in the cement to anchor the positioner relative to the femoral canal;
  means for spacing the femoral hip implant a predetermined distance from the lateral aspect of the femoral canal, wherein the means for spacing comprises a spacing member connected to the body a predetermined distance from the second member, the spacing member engageable with the femoral hip implant and the second member engageable with the lateral aspect of the femoral canal to maintain a predetermined spacing between the femoral hip implant and the lateral aspect of the femoral canal, and
  a projection extending distally from the first member to engage a recess formed in the femoral hip implant.

6. A positioner for retaining a femoral hip implant in a femoral canal, the femoral canal having anterior, posterior, medial, and lateral aspects and a longitudinal axis along the femoral canal from a proximal position near the hip joint to a distal position nearer the knee joint, the femoral hip implant being surrounded at least in part by cement positioned between the femoral hip implant and the femoral canal, the femoral hip implant having a longitudinal axis that in use is approximately parallel to the femoral canal longitudinal axis, and a polished and tapered exterior surface that permits the implant to move relative to the cement and therefore to subside distally into the cement under load, the positioner comprising:
  means for preventing the femoral hip implant from rising out of the femoral canal beyond a predetermined position while permitting subsidence of the femoral hip implant distally into the cement;
  means for anchoring the means for preventing relative to the femoral canal;
  a body including first and second members extending at an angle from one another, the means for preventing including the first member and the means for anchoring including the second member, the first member being positionable over a portion of the femoral hip implant, the second member being positionable in the cement to anchor the positioner relative to the femoral canal; and
  third and fourth members extending from the body, the second, third, and fourth members being positionable in the cement adjacent the lateral, anterior, and posterior aspects of the femoral canal respectively.

7. The positioner of claim 6 wherein at least the third and fourth members are biased inwardly toward the femoral hip implant axis in use to releasably grip the femoral hip implant prior to insertion of the femoral hip implant into the cement.

8. The positioner of claim 6 wherein each of the second, third, and fourth members further comprises a projection extending inwardly toward the femoral hip implant axis in use, the projections being engageable with the exterior surface of the femoral hip implant to maintain a predetermined spacing between the members and the femoral hip implant.

9. A positioner for positioning a femoral hip implant in a femoral canal, the canal having a canal wall and a longitudinal axis extending from an upper position near the hip joint to a lower position near the knee joint, and anterior, posterior, medial, and lateral aspects radially about the axis, the femoral hip implant having a shoulder defining the top of the femoral hip implant, the positioner comprising:
  an "L"-shaped body having a first leg positionable over the shoulder of the femoral hip implant relative to the longitudinal axis and a second leg simultaneously positionable within the canal adjacent the canal wall between the femoral hip implant and the canal wall to maintain a predetermined spacing between the femoral hip implant and the canal wall while permitting downward motion of the implant into the canal.

10. A femoral hip system for implantation with bone cement in a hip joint formed by a femur and a pelvis, the femur having a femoral canal, the system comprising:
  a femoral hip implant having a stem insertable into a femoral canal; and
  a positioner having an anchor member embeddable in bone cement to secure the positioner in the femoral canal adjacent the hip implant, and a retention member engageable with a portion of the femoral hip implant such that it blocks upward motion of the implant out of the canal while permitting downward motion of the implant into the canal during articulation of the joint, the positioner comprising a unitary, "T"-shaped body with legs projecting downwardly from the ends of the "T", the T"-shaped body defining the retention member and the downwardly projecting legs defining the anchor member.

11. The femoral hip system of claim 10 wherein the positioner further comprises a boss projecting downwardly from the "T"-shaped body, the boss being engageable with the stem to space the stem radially a predetermined distance from the legs.

12. A positioner for retaining a femoral hip implant in a femoral canal having a longitudinal axis and a canal wall extending from an upper position near the hip joint to a lower position near the knee joint, and anterior, posterior, medial, and lateral aspects radially about the axis, the positioner comprising:

a first member positionable proximally over a portion of the femoral hip implant; and a second member extending at an angle from the first member, the second member being securable relative to the femoral canal such that the positioner limits upward axial motion of the femoral hip implant while permitting downward axial motion of the femoral hip implant postoperatively during articulation of the joint, the first and second members being angled such that the first member is positionable proximally over a portion of the femoral hip implant while the second member extends around the exterior of the implant to engage a cement mantle surrounding the femoral hip stem, the first member comprising a top and the second member comprising a first leg that curves downwardly from the top approximately 90 degrees, the positioner further including a second leg extending from the top and curving downwardly approximately 90 degrees, and a third leg extending from the top and curving downwardly approximately 90 degrees such that the first, second, and third legs are positionable along first, second, and third sides of the femoral hip implant.

13. The positioner of claim 12 further comprising a boss projecting downwardly from the first member, the legs each curving downwardly approximately parallel to the boss and surrounding the boss.

14. The positioner of claim 13 wherein each leg further comprises a tab extending inwardly toward the boss.

15. A method for positioning a femoral hip implant in a femoral canal, the method comprising:

inserting cement into the femoral canal;

inserting a femoral hip implant into the cement in the femoral canal;

inserting an implant positioner adjacent to the femoral hip implant with an anchor member placed into the cement such that the anchor member becomes firmly attached to the cement upon hardening of the cement and with a retention member positioned above a portion of the implant such that upward motion of the femoral hip implant beyond a predetermined position is limited by abutment of the portion against the retention member while downward subsidence of the femoral hip implant is unimpeded by the positioner during articulation of the hip joint in normal use by a patient, comprising a boss extending downwardly from the retention member, and engaging the boss with the femoral hip implant to space the femoral hip implant a predetermined distance from the anchor member.

16. A method for positioning a femoral hip implant in a femoral canal, the method comprising:

inserting cement into the femoral canal;

inserting a femoral hip implant into the cement in the femoral canal;

inserting an implant positioner adjacent to the femoral hip implant with an anchor member placed into the cement such that the anchor member becomes firmly attached to the cement upon hardening of the cement and with a retention member positioned above a portion of the implant such that upward motion of the femoral hip implant beyond a predetermined position is limited by abutment of the portion against the retention member while downward subsidence of the femoral hip implant is unimpeded by the positioner during articulation of the hip joint in normal use by a patient, the positioner comprising a tab extending inwardly toward the femoral hip implant from the anchor member, and engaging the tab with the femoral hip implant to space the femoral hip implant a predetermined distance from the anchor member.

17. A method for positioning a femoral hip implant in a femoral canal, the method comprising:

inserting cement into the femoral canal;

inserting a femoral hip implant into the cement in the femoral canal;

inserting an implant positioner adjacent to the femoral hip implant with an anchor member placed into the cement such that the anchor member becomes firmly attached to the cement upon hardening of the cement and with a retention member positioned above a portion of the implant such that upward motion of the femoral hip implant beyond a predetermined position is limited by abutment of the portion against the retention member while downward subsidence of the femoral hip implant is unimpeded by the positioner during articulation of the hip joint in normal use by a patient, the anchor member comprising first, second, and third legs extending downwardly from the retention member, and placing the first, second, and third legs in the cement adjacent anterior, lateral, and posterior sides of the femoral hip implant.

* * * * *